United States Patent [19]

Kim

[11] Patent Number: 5,254,474
[45] Date of Patent: Oct. 19, 1993

[54] METHOD OF ASSESSING THERMAL PROCESSING OF FOOD USING INTRINSICALLY-CREATED COMPOUNDS

[75] Inventor: Hie-Joon Kim, Wayland, Mass.

[73] Assignee: The United States of America as represented by the Secretary of the Army, Washington, D.C.

[21] Appl. No.: 660,308

[22] Filed: Feb. 25, 1991

[51] Int. Cl.$^5$ .................. G01N 30/74; G01N 31/00
[52] U.S. Cl. ........................................ 436/1; 436/2; 422/20; 422/26; 426/237
[58] Field of Search ................................... 436/1-2; 422/20-23, 26; 426/237

[56] References Cited

U.S. PATENT DOCUMENTS 3,000,706  9/1961  Royce ................................ 422/55
3,862,824  1/1975  Chapman ............................ 422/56
4,514,361  4/1985  Hirsch ................................ 422/57

OTHER PUBLICATIONS

"Chemical Markers Help Prove Sterility of Food," *Chemical and Engineering News*, May 21, 1990, pp. 39 and 43.

Abstract entitled, "Intrinsic Chemical Markers for HT/ST Processing of Particulate Foods," H. J. Kim, K. R. Conco, M. J. Richardson & I. A. Taub, *Program Abstracts*, 1990 IFT Annual Meeting, Anaheim, Jun. 16–20, 1990, p. 135.

Abstract entitled, "Intrinsic Chemical Marker for Aseptic Processing of Particulate Foods," H. J. Kim, K. R. Conca, M. J. Richardson, and I. A. Taub, presented at American Chemical Society, 199th National Meeting held on Apr. 22, 1990.

"Intrinsic Chemical Markers for Thermal Processing of Particulate Foods," Hie Joon Kim and Irwin A. Taub, *Proceedings of the Third Natick Science Symposium*, 5–6 Jun. 1990, Aug. 1990, pp. 207–218.

"Relationship of Sugar Degradation to Detrimental Changes in Citrus Juice Quality," H. S. Lee and S. Nagy, *Food Technology*, Nov. 1988, pp. 91–97.

*Primary Examiner*—Lyle A. Alexander
*Attorney, Agent, or Firm*—Richard J. Donahue

[57] ABSTRACT

A method of assessing the degree of thermal processing of a food by preparing an aqueous medium including at least a portion of the processed food and monitoring the medium for the presence of a thermally produced compound not present in the unprocessed food to indicate the exposure of the food to heat.

11 Claims, 5 Drawing Sheets

METHOD OF ASSESSING THERMAL PROCESSING OF FOOD USING INTRINSICALLY-CREATED COMPOUNDS

STATEMENT OF GOVERNMENT INTEREST

The invention described herein may be manufactured, used and licensed by or for the Government for Governmental purposes without the payment to us of any royalties thereon.

FIELD OF INVENTION

This invention relates to a method of assessing thermal processing of foods using intrinsically-created compounds which are indicators of the integrated time-temperature exposure of food to heat.

BACKGROUND OF INVENTION

Industrial thermal processing of foods has, until recently, been a batch process, using cans or other sealed containers. Recently, continuous aseptic processing techniques have been employed for continuously sterilizing foods and beverages while flowing; the processed food is then packaged in sterilized containers. In the aseptic process, the food is sterilized at a relatively high temperature of between 265° F. and 300° F. for a relatively short time.

In thermally processing food, it is critical that the food or the process be monitored to ensure sterility. In the batch processing techniques, the achievement of sterility was commonly indicated using color-change indicators engineered to create a color change at a certain given temperature, or after a certain time-temperature exposure. See, for example, U.S. Pat. Nos. 4,514,361, 3,862,824, and 3,000,706. These color change indicators were acceptable for batch sterilization because the entire food containers were subjected to sterilization after sealing. Accordingly, the color change indicators could be applied directly to the containers, or could be placed in the batch processor along with the containers being processed.

Another approach at estimating sterility has been to use mathematical modeling. However, modeling is subject to uncertainty as a result of the assumptions which have to be made in aseptic processing due to the difficulty of measuring the temperature within the flowing stream of liquid food, or at the center of a moving food particulate. As a result, modeling techniques require conservative assumptions of physical parameters, often leading to severe overprocessing of food.

There have also been attempts at using microbiological techniques to determine sterility. For example, particulate foods have been inoculated with thermophilic bacteria as a bioindicator of aseptic processing. The equivalent lethality delivered to C. Botulinum, a standard measure of sterility, is estimated based on the decrease in bacteria population. However, this procedure requires the careful inoculation of the particulates before testing, and bacteria counting after testing, making the entire procedure tedious and subject to experimental uncertainties Moreover, the extent of food overprocessing is difficult or impossible to assess, because once the entire microbial population is destroyed, no further changes can be detected.

There have also been a number of attempts to estimate the sterility of aseptically processed foods by measuring the thermal destruction of compounds added to food before processing. However, these techniques suffer from a number of drawbacks which make them poor indicators of food sterility. For one, typical chemical reaction in foods is either too fast or too slow to be a useful indicator of sterility. For example, destruction of heat-resistant enzymes such as peroxidase is complete in about two minutes at 212° F.; such a fast reaction cannot be used to indicate the degree of thermal processing at high-temperature aseptic conditions. On the other hand, destruction of nutrients such as ascorbic acid and thiamin is much slower than the thermal death of bacteria spores at the high aseptic processing temperatures. For example, the microbial lethality rate at aseptic processing temperatures is about ten times that of the rate at retort temperature, whereas the destruction of thiamin is only about two times faster at the higher temperature. Accordingly, the relatively short time-high temperature aseptic processing conditions will lead to little change in the thiamin concentration, making accurate testing extremely difficult.

SUMMARY OF INVENTION

It is therefore an object of this invention to provide a method for assessing the degree of thermal processing of both liquid and particulate foods at aseptic processing conditions.

It is a further object of this invention to provide such a method which is an accurate indicator of the integrated time-temperature exposure of the food.

It is a further object of this invention to provide such a method which is a direct indicator of food sterility.

It is a further object of this invention to provide such a method which is easy to perform.

It is a further object of this invention to provide such a method which does not require the addition of a chemical or microbiological indicating agent.

It is a further object of this invention to provide such a method in which the compound indicative of sterility is intrinsically-created.

It is a further object of this invention to provide such a method in which the concentration of the compounds indicative of thermal processing increase as the integrated time-temperature exposure increases.

It is a further object of this invention to provide such a method in which the compound is easy to detect.

It is a further object of this invention to provide such a method which uses readily available equipment and testing procedures.

It is a further object of this invention to provide such a method in which the compound indicative of sterility is extremely stable.

This invention results from the realization that the degree of aseptic thermal processing of foods can be easily and accurately determined by monitoring the processed foods for the presence and relative concentration of intrinsically thermally produced compounds.

This invention features a method of assessing the degree of thermal processing of a food including the steps of preparing an aqueous medium including at least a portion of the processed food, and monitoring the medium for the presence of a thermally produced compound typically not present in measurable quantities in the unprocessed food to indicate the exposure of the food to heat. This method may be employed for monitoring the degree of thermal processing of foods which are pure liquids, and foods which contain particulates.

The aqueous medium may be prepared by homogenizing the food, including some or all of the particulates, with water, to prepare an aqueous extract of soluble compounds. The extract is preferably filtered to remove insoluble materials. The aqueous medium is preferably monitored by performing anion exclusion chromatography to produce an effluent containing the thermally produced compound, and analyzing the effluent for the presence and relative concentration of the thermally produced compound Since the compound is typically not present in unheated food, the test is an extremely sensitive indicator of food thermal processing. Preferably, the analysis is accomplished with ultraviolet absorption spectroscopy. The eluant is preferably acidic; a dilute sulfuric acid eluant may be employed. The ultraviolet absorption detection may be accomplished with a photodiode array detector for scanning over time a wide ultraviolet absorption band, in which case the output of the photodiode array may be provided to a three-dimensional graphical output device for plotting absorption wavelength and strength versus time.

The thermally produced compound may be made by thermal degradation of a precursor taken from various groups, including fructose and glucose. One such thermally produced compound is hydroxymethyl furfural. Another thermally produced compound has an ultraviolet absorption maximum at 298 nanometers and a molecular weight of approximately 180.

The integrated time-temperature exposure of the food as well as the sterility value of the food may be determined from the relative compound concentration.

DISCLOSURE OF PREFERRED EMBODIMENT

Other objects, features and advantages will occur to those skilled in the art from the following description of a preferred embodiment and the accompanying drawings, in which.

This invention may be accomplished in a method of assessing the degree of thermal processing of a food which includes the steps of preparing an aqueous medium of at least part of the processed food, including some of the liquid or some or all of one or more particulates contained within the processed food, and monitoring the aqueous medium for the presence and relative concentration, as indicated by the relative absorption, of an intrinsically-produced water-soluble compound or compounds not present in the unprocessed food to indicate the integrated time-temperature exposure of the food to heat, and so its sterility.

Figure 1:
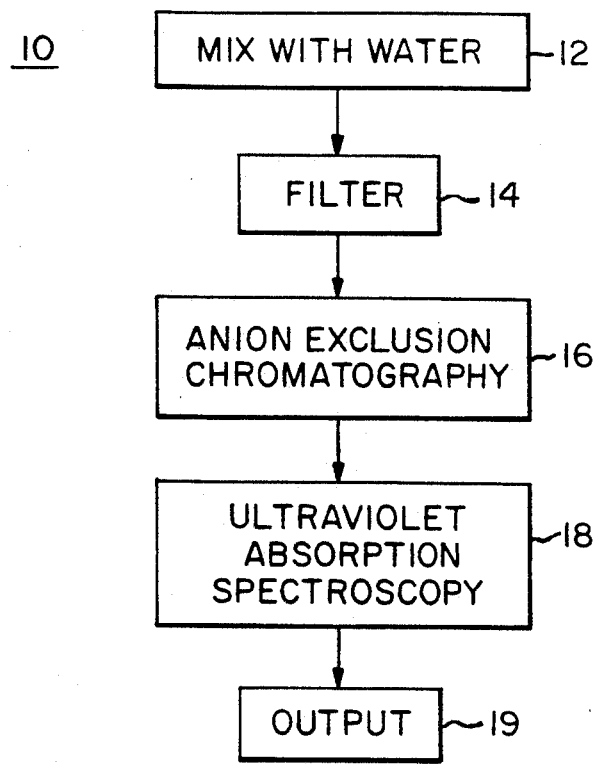
FIG. 1 is a schematic representation of the method of this invention.

There is shown in FIG. 1 the basic steps of method 10 according to this invention for detecting the presence and relative concentration of an intrinsically-produced, water-soluble compound, or marker, indicative of the integrated time-temperature exposure of an aseptically processed food. In step 12, the heated food to be tested, which may be a liquid food such as fruit juice, or a food containing particulates such as chicken stew, is homogenized with water to extract the soluble compounds. Preferably, the extraction is performed by rapid homogenization with a Polytron high speed homogenizer made by Brinkmann Instruments Company of Westbury, N.Y. In step 14, the insoluble materials are removed by filtration. A membrane filter having a pore size of about 0.2 to 1.0 microns may be used; a preferred type of filter is a 0.45 micron membrane filter such as a Nylon 66 0.45 micron filter unit made by Alltech Associates, Deerfield, Ill. The filtrate containing the water-soluble, intrinsically produced marker compound or compounds is then analyzed for the presence and/or relative concentration of the marker(s). A preferred analysis is a combination of anion exclusion chromatography, step 16, followed by ultraviolet absorption spectroscopy, step 18, of the stream leaving the chromatography column Anion exclusion chromatography such as that performed herein is explained in some detail in U.S. Pat. No. 4,780,417, incorporated herein by reference. Alternatively, other known means of detecting the presence and concentration of water soluble compounds, such as mass spectrometry, may be employed.

Preferably, an anion exclusion apparatus such as the Wescan Ion Chromatography System (Alltech Associates, Deerfield, Ill.) is employed, with a stainless steel tube column of 7.8 millimeter internal diameter by 100 millimeter length using a sulfonated copolymer of styrene and divinylbenzene having about 1 to 8 percent divinylbenzene cross-linking. The eluant is preferably a weak acid such as 5 millimolar sulfuric acid delivered at 1 milliliter per minute. A preferred method of introducing the soluble compounds being analyzed is an injection apparatus such as the Rheodyne 7125 Injection Valve, Cotati, Calif., which delivers from 20 to 100 microliters of filtrate into the chromatography column.

The stream leaving the chromatography column is routed to an ultraviolet absorption spectrometer Preferably, a Waters 990 photodiode array detector made by Millipore Corporation, Milford, Mass., is used along with a three dimensional graphical output (contour diagram) as further explained below. The absorption is detected by a photodiode array having approximately 200 diodes, each detecting simultaneously at different wavelengths in the ultraviolet range of about 190 to 400 nanometers. The spectral analyzer is able to sample the output of the array at a desired time interval from a fraction of a second up to seconds in time. The spectral analysis is outputted, step 19, in the form of a graphical analysis detailing the absorption strength versus time over the entire monitored wavelength band. Alternatively, a more narrow-band detector may be employed when a single marker compound having an absorption peak at a known wavelength is being monitored. One output device comprises a printer/integrator such as the Spectra Physics SP4200 computing integrator made by Spectra Physics, San Jose, Calif.

EXAMPLE ONE

Figure 2:
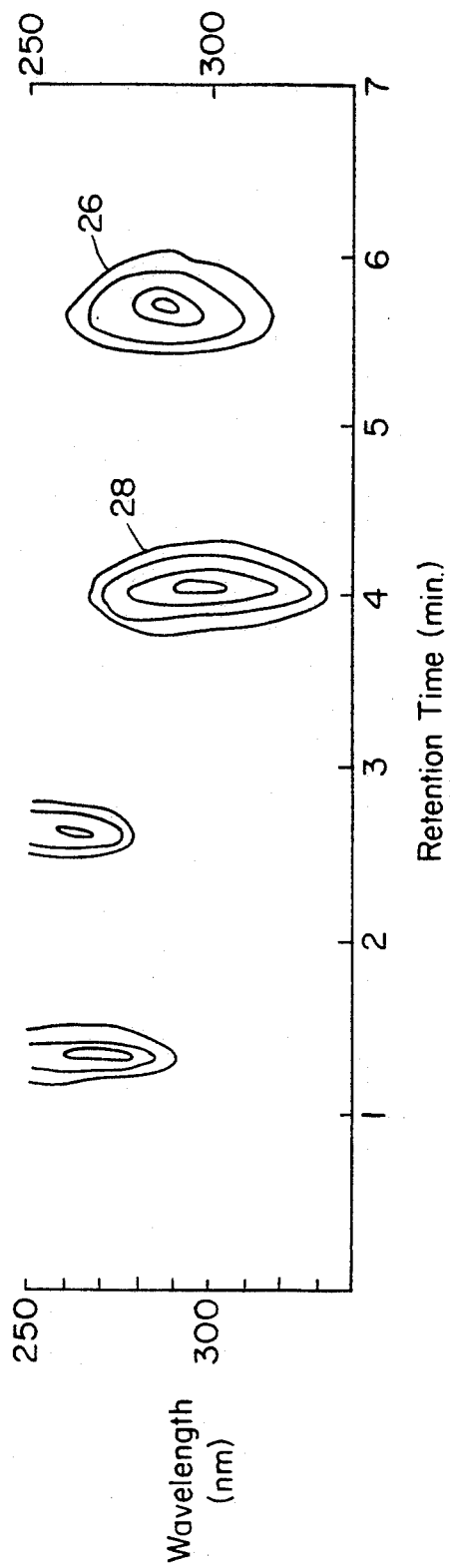
FIG. 2 is a contour diagram from a three-dimensional representation of an output from the method of FIG. 1 for two intrinsically-created chemical markers in heated beef.

FIG. 2 depicts an output representing detection of two intrinsically-created compounds from a sample of heated beef particulate which had been subjected to the testing procedure of FIG. 1. The nature of the contour diagram output is explained below in conjunction with FIGS. 4A-4C. As shown, there were two separate absorption maxima at a retention time of about four minutes and a retention time of about five and three-quarters minutes, indicating that two separate intrinsically thermally-produced compounds were created from heating of the meat particle; neither artifact was present in the same tests run on the beef before heating (absorbance measurement limit approximately 0.0001 AU). The artifacts eluting at just over one minute and just over 2.5 minutes were background absorption caused by the plethora of water soluble compounds present in cooked meats. It has been found from extensive testing of different food types that the marker represented by area 28 is produced from vegetables, fruits and meats whereas the marker represented by area 26 is produced from meats only.

Figure 3:
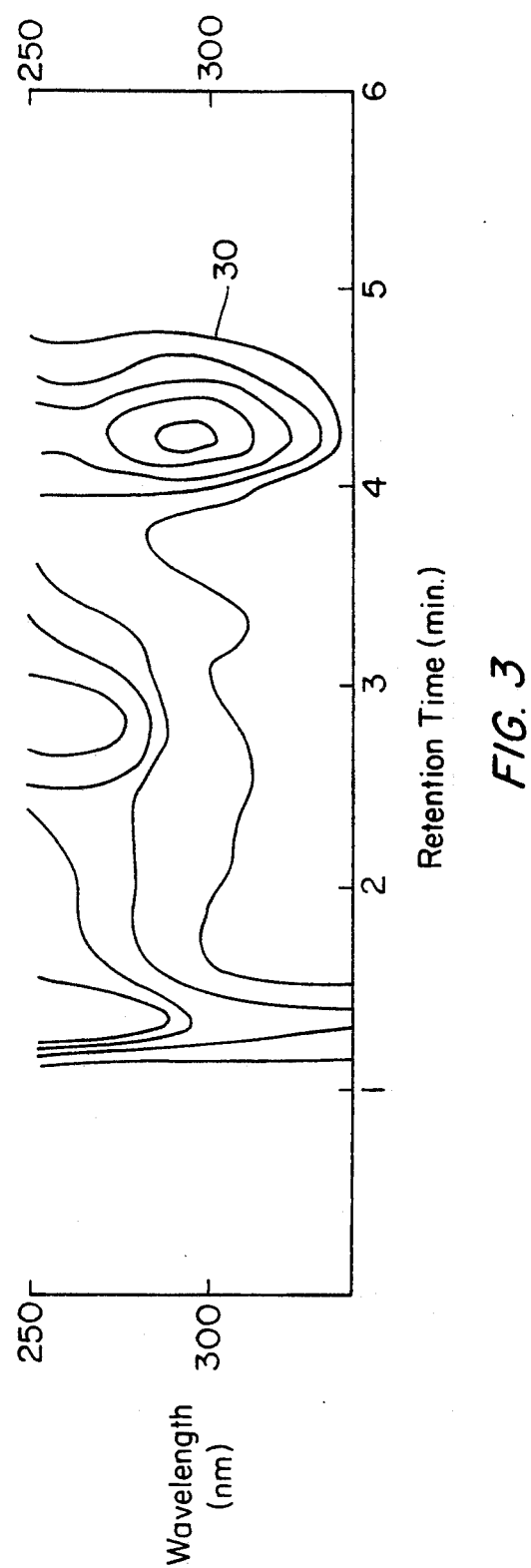
FIG. 3 is an output similar to that of FIG. 2 for a chemical marker of FIG. 2 found in a thermally processed vegetable.

This conclusion is bolstered by the output of FIG. 3, which is for a sample of heated broccoli, showing a single compound eluting at about 4 to 5 minutes, without the second compound eluting at between 5 and 6 minutes. More particularly, when a 7.8 by 100 millimeter column as described above is used with five millimolar sulfuric acid eluant at a one milliliter per minute flow rate, the retention time for the compound, represented by area 28, FIG. 2, produced in vegetables, fruits and meats is 4.0 to 4.5 minutes, and the retention time for the compound produced from meats only, represented by area 26, FIG. 2, is 5.5 to 6.0 minutes. These results have been obtained by injecting between 20 and 50 microliters of the filtered extract into the chromatograph.

A purified form of the marker produced from vegetables, fruits and meats has been found to have an absorption maximum at 298 nanometers, whereas the absorption maximum for the other marker compound produced from meats only is about 285 nanometers. Accordingly, these markers could be assayed by using fixed wavelength ultraviolet detectors set at about 285 and 298 nanometers, respectively. Using gel filtration chromatography, it has been found that the marker produced from vegetables, fruits and meats and having an absorption maximum at 298 nanometers has a molecular weight of approximately 180. Further, it has been shown that fructose upon heating yields that marker compound. Accordingly, the molecular weight of the compound is considered to be just slightly less than the molecular weight of fructose (180 daltons). The other marker compound with an output shown in FIG. 2, produced from meats only, has been found to have a molecular weight of about 180 as well.

EXAMPLE TWO

Figure 4C:
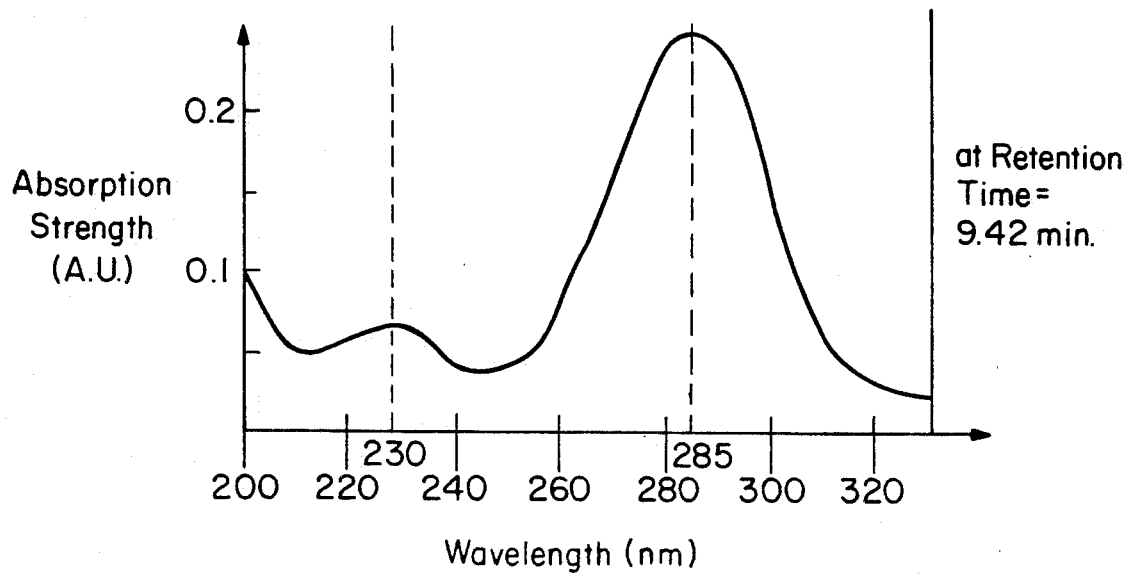
FIG. 4C is a segment of the output of FIG. 4A taken at a retention time of 9.42 minutes.
Figure 4A:
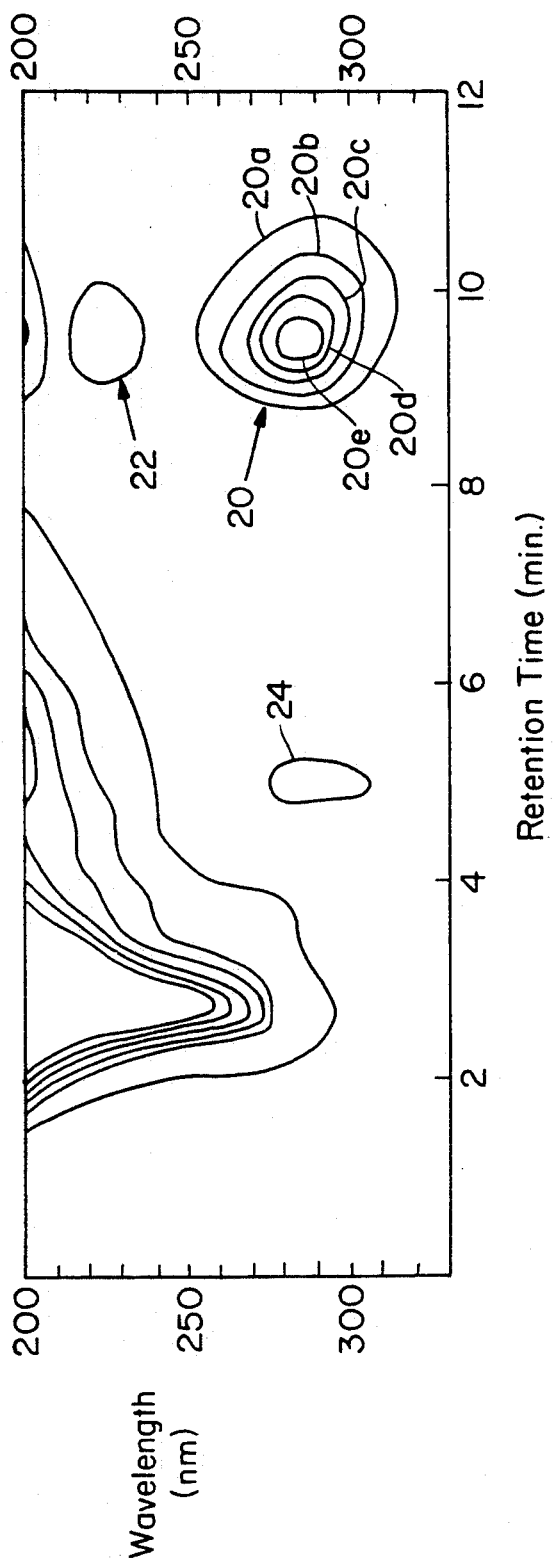
FIG. 4A is a contour diagram from a three-dimensional representation similar to that of FIG. 2 for a third chemical marker from heated orange.
Figure 4B:
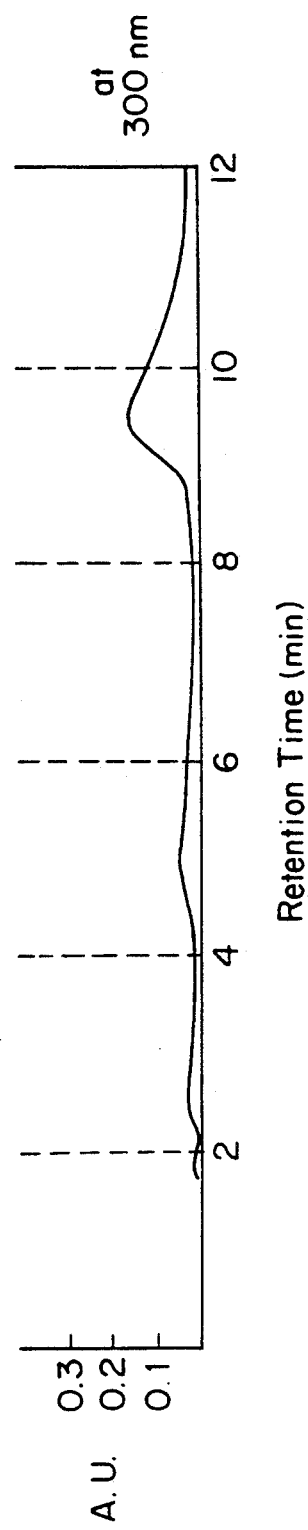
FIG. 4B is a segment of the output of FIG. 4A taken at 300 nanometers.

FIGS. 4A through 4C detail three forms of output for detection of an intrinsically produced marker compound produced by thermal degradation of compounds found in fruits and fruit juices. FIG. 4A depicts a three dimensional graphical spectrochromatogram, which is similar to a contour map, having the absorption wavelength on the y axis, the chromatographic column retention time on the x axis, and absorption strength in absorbance on the z axis. The output is taken from the computer and printed on a NEC Pinwriter CP6, NEC Information Systems, Boxborough, Mass. In the example of FIGS. 4A through 4C, a sample of a heated orange was tested. The output shows a compound having a column retention time of about 8 to 10 minutes having two ultraviolet absorption maxima, at 230 and 285 nanometers as shown by output areas 20 and 22.

As an example of the contour-diagram representation of the three dimensional nature of the output, area 20 includes concentric contour lines, each representing a change in absorption level, labelled 20a through 20e; the area between lines 20a and 20b, shaded light green in the color output preferably employed, represents an absorption of approximately 0.04 to 0.08 AU. The area between lines 20b and 20c, black in the colored output, represents an absorption of from approximately 0.08 to 0.12 AU. The area between lines 20c and 20d, orange in the colored output, represents an absorption of approximately 0.12 to 0.18 AU. The area between lines 20d and 20e, green in the output, represents an absorption of between approximately 0.18 and 0.22 AU. Finally, the area inside of line 20e, red in the output, represents an absorption of from approximately 0.22 to 0.26 AU. The apparatus employed had a lower detection limit of about 0.0001 absorption units The three dimensional nature of the output is more easily understood in reference to FIGS. 4B and 4C, in which FIG. 4B is a cross section parallel to the x axis taken at 300 nanometers absorption wavelength, showing a very slight absorption increase at about five minutes retention time, and the large increase at about nine to ten minutes retention time. The cross section of FIG. 4B is not taken through the center or high point of the artifact 20, which occurs at about 285 nanometers. Such a cross section parallel to the y axis is shown in FIG. 4C, which is taken at a retention time of 9.42 minutes This output depicts the two absorption maxima of the compound having a retention time of about 9.42 minutes at 230 and 285 nanometers. This compound, having a retention time of about eight to ten minutes under the conditions described above, and having ultraviolet absorption maxima at 230 and 285 nanometers, has been observed in many types of aseptically processed fruit juices as well as portions of fruits such as apple and orange which have been heated. The relative concentration of this compound represented by the measured absorption has been found to be higher at the surface of heated particulate foods than at the center of the particulates. As described in more detail below, this compound has been identified as hydroxymethyl furfural, a thermal degradation product of both glucose and fructose.

The manner in which the precursors of hydroxymethyl furfural, as well as the identification of hydroxymethyl furfural as one of the intrinsically thermally-produced marker compounds indicative of the degree of the thermal processing of foods, is as follows A compound having the double absorption maxima at 230 and 285 nanometers and a retention time of about 9.42 minutes was detected in heated orange and apple. Pure glucose, fructose, sucrose and ascorbic acid were tested to see if they were the precursors for this marker compound The tests were performed by heating the pure compounds and performing the above-described analysis on them in an attempt to detect the presence of the marker compound. It was found that both glucose and fructose, when heated, created the compound having the correct characteristics. Hydroxymethyl furfural was then identified as being a potential thermal degradation product of both glucose and fructose. A solution of that compound was then analyzed, and found to have the correct retention time and absorption maxima.

These results were checked by subjecting both the pure and heated forms of fructose and hydroxymethyl furfural to a gel filtration separation method. The pure fructose was separated as the twenty-second fraction, and the marker compound from the heated fructose separated as the twenty-fifth fraction, as was pure hydroxymethyl furfural. Then, samples of soluble compounds of unheated and heated orange were subjected to the same gel filtration method and it was found that a component of the unheated sample separated at fraction twenty-two, which was converted to hydroxymethyl furfural upon heating, indicating that the unheated fruit contained a compound having the same molecular weight as fructose The heated orange samples had separation at fraction twenty-five, indicating the presence of hydroxymethyl furfural.

Figure 5:
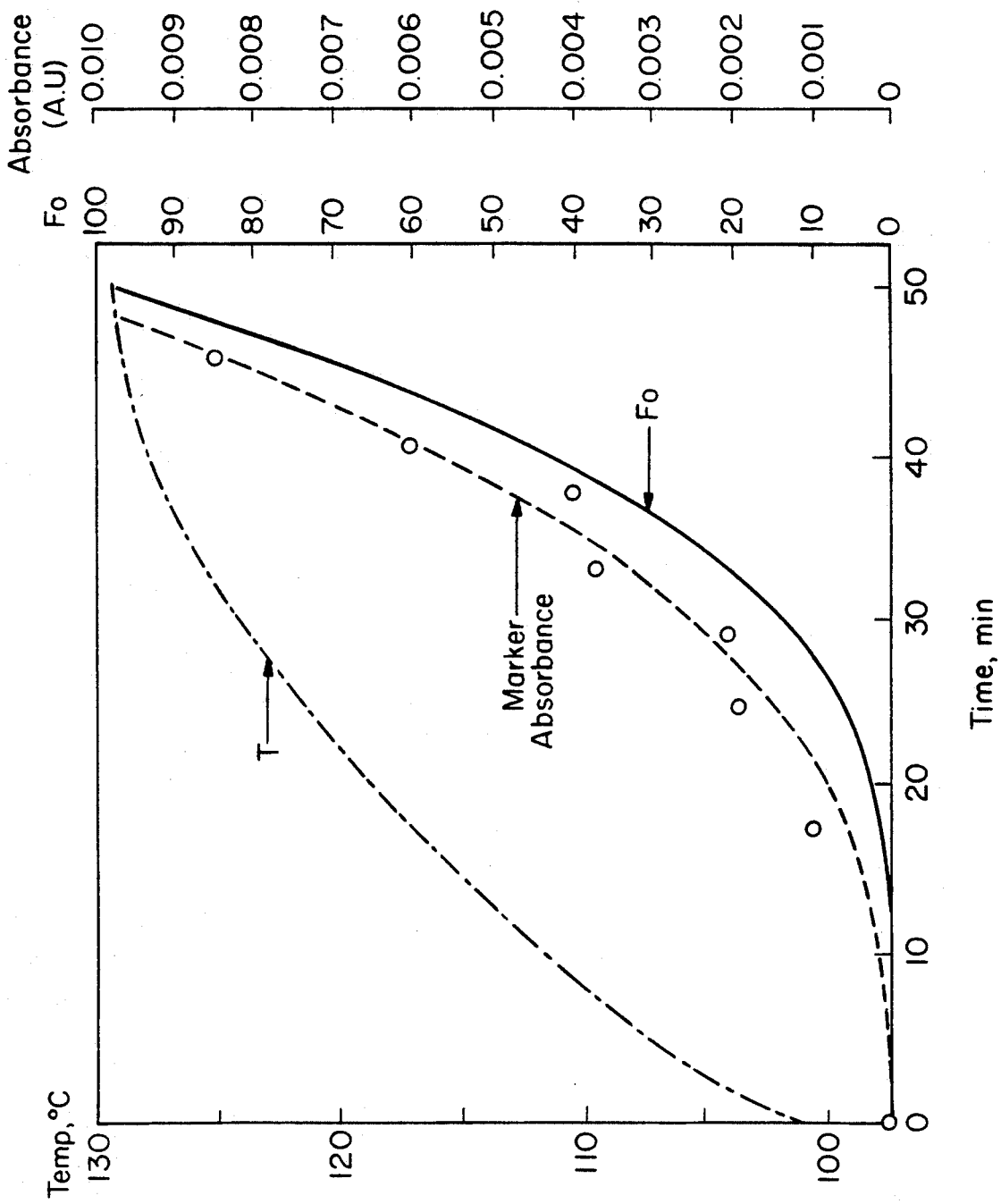
FIG. 5 is a representation of the relationship between the relative absorbance of a chemical marker and the food sterility.

FIG. 5 depicts the relative concentration of the marker compound produced from vegetables, fruits and meats, having an absorption maximum at 298 nanometers and a molecular weight of about 180, versus the sterility ($F_0$) and temperature of a heated food sample. The compound is not present in measurable quantities in the unheated food. The information charted in FIG. 5 was derived from eight vials of a potato puree which were heated together in a 130° C. oven. The puree of potato was prepared by blending 160 grams of cut potatoes with 120 milliliters of hot brine including 3.4% sugar and 1.7% salt. Ten 20 milliliter glass vials were filled with the puree, sealed with a rubber septum and aluminum cap, and placed in a laboratory oven preheated to 130° C. Two of these vials were used for temperature measurement. A thermocouple was pushed through the rubber septum and placed at the center of one vial. Another thermocouple was placed midway between the wall and the center of the second vial. The temperature charted in FIG. 5 is the average temperature at the two locations. At the times indicated along the marker absorbance curve, a vial was withdrawn from the oven and quickly cooled with cold water. The contents of the vial were then homogenized with a five fold excess of water and the extract was filtered through a 0.45 micron membrane filter. The relative absorbance of the marker in the filtrate was determined as described. The results indicate that this marker is useful as a time-temperature integrator of thermal processing of foods such as fruits, vegetables and meats.

The $F_0$ values charted were calculated from the temperature measured by thermocouple according to the relationship:

$$F_0 = 10(T-121.1)/10$$

where temperature is in degrees Centigrade. $F_0$ is the thermal death time in minutes required to reduce the microbial population by a factor of $10^{12}$ at 250° F. for a spore-forming microorganism whose thermal death time is decreased by a factor of 10 when temperature is increased by 18° F. (C. Botulinum). Accordingly, the accumulated $F_0$ value is the index of sterility at the site of temperature measurement. A good correlation with $F_0$ is a key feature of a chemical marker since the objective is to assess $F_0$ from measurement of intrinsically produced marker concentration. As shown in FIG. 5, the absorbance, and so the concentration of the marker, parallels the $F_0$ value. As a result, the marker absorbance value is a useful indicator of both thermal processing and sterility.

The formation of this marker from its precursor was examined as follows. The aqueous extract from a heated broccoli sample was fractionated on a 1.0 by 42 centimeter gel filtration column packed with Bio-Gel P-2 made by Bio-Rad, Richmond, Calif., having a molecular weight cutoff of 2000 daltons, at a flow rate of 10 milliliters per hour. A 1.71 milliliter volume was collected per fraction. The collected fractions were analyzed for the marker by the chromatography/ultraviolet absorption system described above, and the marker was found in fraction 24.

In order to investigate the precursor, an aqueous extract from the unheated broccoli was fractionated on the same filtration column, and the collected fractions were heated in sealed glass tubes. When the heated fractions were analyzed for the marker, only fraction 22 yielded the marker. When the aqueous extract was heated in the sealed capillary tube, an exponential increase in the marker concentration to a limiting value was observed. When the log of the difference between the limiting value and the observed value was plotted against heating time, a linear relationship was obtained. This observed first-order behavior of the reaction indicates that the reaction rate is solely dependent on the precursor concentration. Since thermal death of bacterial spores is also represented by a first order process, it is apparent that the absorbance (relative marker concentration) is an appropriate indicator of the integrated time-temperature heat exposure and so sterility.

EXAMPLE THREE

Figure 6:
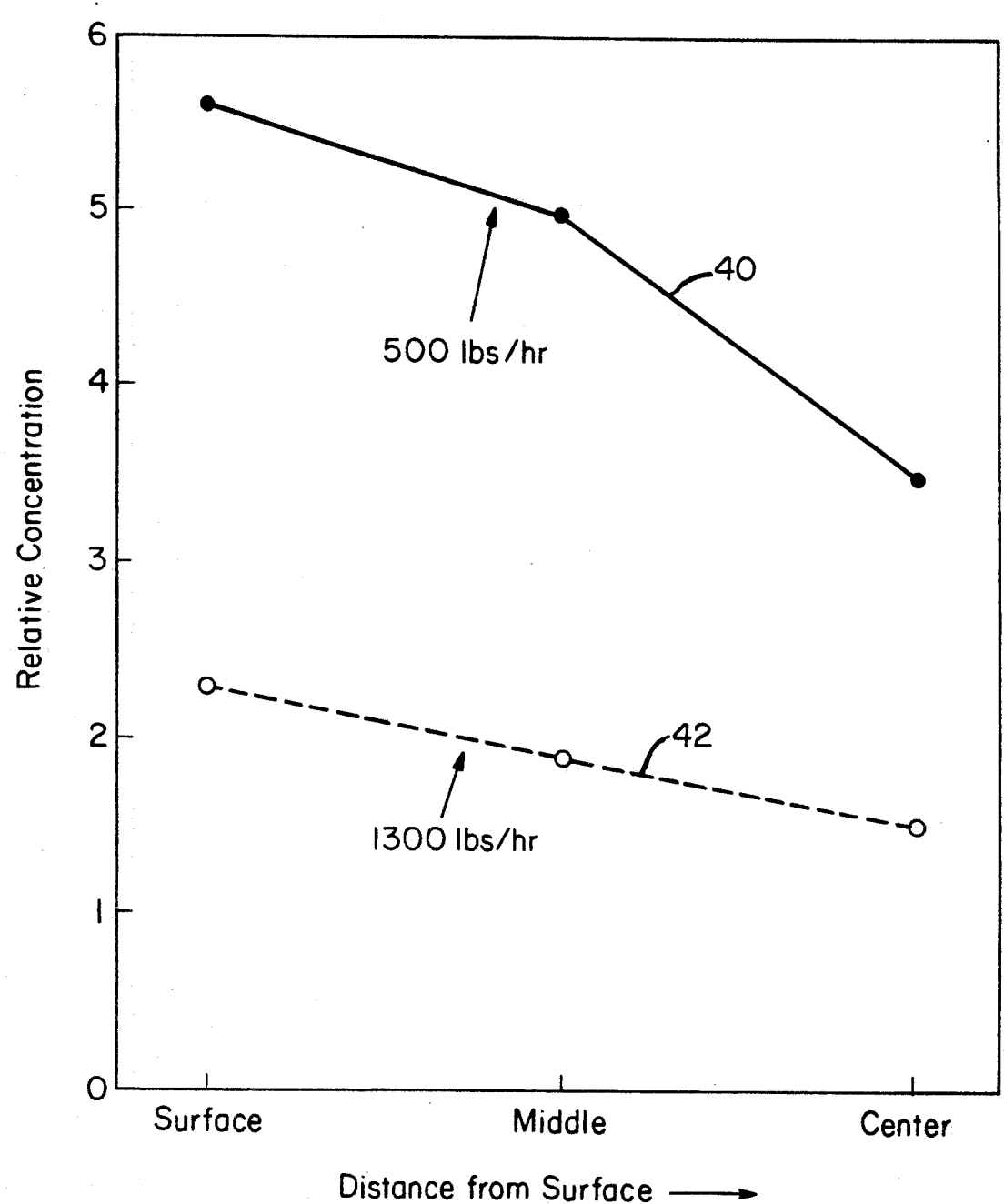
FIG. 6 is a graph depicting the relative concentration of a chemical marker in two batches of aseptically processed particulate-containing food.

FIG. 6 depicts the relative concentration of the marker produced only in meats and having an absorption maximum at about 285 nanometers, a molecular weight of about 180, and a retention time of about 5.5 to 6 minutes in the chromatography column described above. The plotted results are for two aseptic processing runs of chicken stew including particulate meat; the aseptic processing took place at 265° F. at two different flow rates—500 pounds per hour and 1300 pounds per hour. Samples of the chicken meat particulates were frozen with ice immediately following the aseptic processing. The meat pieces were then divided with a razor blade into surface, middle and center portions of approximately equal thickness from a number of particles, and the portions from several meat pieces were pooled together. The aqueous extract from these meat portions was concentrated by freeze drying and redissolving in a small volume of five millimolar sulfuric acid solution to increase the concentration of the marker.

In both runs, there was a definite relative concentration gradient for the marker (as measured by absorbance) decreasing gradually in the direction of heat transfer from the surface to the center. This gradient is believed to reflect the temperature gradient within the meat. Also, the marker concentration was higher at the lower flow rate (longer aseptic processing residence time). The direct proportionality between the residence time and relative marker concentration suggests that the marker is a good indicator of heat exposure. The higher relative marker concentration at the center of the particulates processed at the lower flow rate as opposed to those processed at the higher flow rate suggests that the lethality at the center of a food particulate will be determined primarily by external parameters such as temperature and flow rate, as opposed to heat transfer characteristics inherent in the food being processed, which are harder to control.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A method of determining the relative sterility of thermally processed foods, comprising:
    homogenizing at least a portion of a thermally-processed food with water to prepare an aqueous extract of soluble compounds, including thermally-produced soluble compounds;
    subjecting said aqueous extract to anion exclusion chromatography with an acidic eluant to create an eluted stream;
    measuring over time the ultraviolet absorbance of said soluble compounds in said eluted stream; and
    determining from said absorbance of one or more of said thermally-produced soluble compounds having an absorption maximum at approximately 285 or approximately 298 nanometers an indication of the relative sterility of the food.

2. A method of assessing the relative sterility of thermally processed foods comprising the steps of:
    preparing an aqueous medium which includes at least a portion of the thermally processed food; and
    monitoring said medium for the presence of an intrinsic thermally produced compound having an absorption maximum at approximately 285 nm or approximately 298 nm indicative of the sterility of the food;
    said step of monitoring said medium including subjecting said aqueous medium to anion exclusion chromatography to produce an effluent containing said thermally produced compound;
    said step of monitoring said medium further including analyzing said effluent for the presence of said thermally produced compound;
    said analyzing said effluent including ultraviolet absorption spectroscopy of said effluent.

3. A method of assessing the relative sterility of thermally processed foods comprising the steps of:
    preparing an aqueous medium which includes at least portion of the thermally processed food; and
    monitoring said medium for the presence of an intrinsic thermally produced compound indicative of the sterility of the food;
    said thermally produced compound being hydroxymethyl furfural.

4. A method of assessing the relative sterility of thermally processed foods comprising the steps of:
    preparing an aqueous medium which includes at least a portion of the thermally processed food; and
    monitoring said medium for the presence of an intrinsic thermally produced compound having absorption maxima at approximately 230 nm and 285 nm indicative of the sterility of the food;
    said thermally produced compound being produced by thermal degradation of a precursor taken from the group including fructose and glucose.

5. A method of assessing the relative sterility of thermally processed foods comprising the steps of:
    preparing an aqueous medium which includes at least a portion of the thermally processed food; and
    monitoring said medium for the presence of an intrinsic thermally produced compound indicative of the sterility of the food;
    said thermally produced compound having an ultraviolet absorption maximum at approximately 285 nm.

6. A method of determining the relative sterility of different portions of thermally-processed particulate-containing foods, comprising:
    homogenizing a portion of a food particulate with water to prepare an aqueous extract;
    filtering said extract to remove insoluble materials to leave an aqueous extract to remove insoluble materials to leave an aqueous extract of soluble compounds, including thermally-produced soluble compounds;
    directing said aqueous extract through an anion exclusion chromotography column using an acidic eluant to produce an eluted stream;
    exposing said eluted stream to ultraviolet light;
    monitoring over time said ultraviolet absorption of said soluble compounds of said aqueous extract; and
    determining from said absorption of one or more of said thermally-produced soluble compounds having an absorption maximum at approximately 285 or approximately 298 nanometers an indication of the sterility value of the food particulates.

7. The method of claim 6 in which said ultraviolet-exposed, eluted stream is monitored with a photodiode array.

8. A method of assessing the relative sterility of thermally processed foods comprising the steps of:
    preparing an aqueous medium which includes at least a portion of the thermally processed food; and
    monitoring said medium for the presence of an intrinsic thermally produced compound indicative of the sterility of the food;
    said thermally produced compound having an ultraviolet absorption maximum at 298 nm.

9. The method of claim 8 in which said thermally produced compound has a molecular weight of approximately 180.

10. A method of assessing the relative sterility of thermally processed foods comprising the steps of:
    preparing an aqueous medium which includes at least a portion of the thermally processed food; and
    monitoring said medium for the presence of an intrinsic thermally produced compound indicative of the sterility of the food,
    said thermally produced compound having ultraviolet absorption maxima at approximately 230 and 285 nm.

11. The method of claim 10 in which the precurser for said thermally-produced compound present in the uncooked food is taken from the group including glucose and fructose.

* * * * *